United States Patent
Xue et al.

(10) Patent No.: US 12,152,264 B2
(45) Date of Patent: Nov. 26, 2024

(54) PHOSPHINOTHRICIN DEHYDROGENASE MUTANT, GENETICALLY ENGINEERED BACTERIUM AND ONE-POT MULTI-ENZYME SYNCHRONOUS DIRECTED EVOLUTION METHOD

(71) Applicant: ZHEJIANG UNIVERSITY OF TECHNOLOGY, Hangzhou (CN)

(72) Inventors: Yaping Xue, Hangzhou (CN); Feng Cheng, Hangzhou (CN); Jumou Li, Hangzhou (CN); Qinghua Li, Hangzhou (CN); Yuguo Zheng, Hangzhou (CN); Shuping Zou, Hangzhou (CN); Jianmiao Xu, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 494 days.

(21) Appl. No.: 17/604,412

(22) PCT Filed: Dec. 26, 2020

(86) PCT No.: PCT/CN2020/139770
§ 371 (c)(1),
(2) Date: Oct. 16, 2021

(87) PCT Pub. No.: WO2022/001038
PCT Pub. Date: Jan. 6, 2022

(65) Prior Publication Data
US 2022/0307061 A1    Sep. 29, 2022

(30) Foreign Application Priority Data

Jun. 30, 2020 (CN) .......................... 202010614951.3

(51) Int. Cl.
C12P 13/04 (2006.01)
C12N 1/20 (2006.01)
C12N 15/52 (2006.01)
C12N 15/70 (2006.01)

(52) U.S. Cl.
CPC .............. *C12P 13/04* (2013.01); *C12N 1/20* (2013.01); *C12N 15/52* (2013.01); *C12N 15/70* (2013.01); *C12Y 101/01047* (2013.01); *C12Y 102/01002* (2013.01); *C12Y 104/01004* (2013.01); *C12N 2800/101* (2013.01)

(58) Field of Classification Search
CPC ........... C12P 13/04; C12N 1/20; C12N 15/52; C12N 15/70; C12N 2800/101; C12N 9/0016; C12N 15/1058; C12N 9/0006; C12N 9/0008; C12Y 101/01047; C12Y 102/01002; C12Y 104/01004; C12R 2001/19; C12R 2001/39; C40B 40/02; C40B 40/08

See application file for complete search history.

(56) References Cited

FOREIGN PATENT DOCUMENTS

| CN | 108588045 A | 9/2018 |
| CN | 109609475 A | 4/2019 |
| CN | 110885803 A | 3/2020 |
| WO | WO2019192505 | 10/2019 |

OTHER PUBLICATIONS

NCBI Accession No. VV83255.1 (Sep. 12, 2019, 1 page) (Year: 2019).*
UniProt Accession No. A0A5E7AX49_PSEFL (1 page, Nov. 13, 2019) (Year: 2019).*

* cited by examiner

*Primary Examiner* — David Steadman
*Assistant Examiner* — Joseph Spangler
(74) *Attorney, Agent, or Firm* — Jiwen Chen; Joywin IP Law PLLC

(57) ABSTRACT

Disclosed are a phosphinothricin dehydrogenase mutant, a recombinant bacterium and a one-pot multi-enzyme synchronous directed evolution method. The phosphinothricin dehydrogenase mutant, with an amino acid sequence as shown in SEQ ID No.1, is obtained by mutating alanine at position 164 to glycine, arginine at position 205 to lysine, and threonine at position 332 to alanine in a phosphinothricin dehydrogenase derived from Pseudomonas fluorescens. The recombinant bacterium is obtained by introducing a gene encoding the phosphinothricin dehydrogenase mutant into a host cell. The host cell can also incorporate a gene encoding a glucose dehydrogenase or a gene encoding a formate dehydrogenase to undergo synchronous directed evolution to achieve double gene overexpression. The one-pot multi-enzyme synchronous directed evolution method of the present invention can screen recombinant bacteria with greatly improved activity. Compared with other catalysis processes such as the transaminase method, the method for preparing L-PPT of the present invention features relatively simple process, high conversion of raw materials of up to 100%, and high stereo selectivity.

8 Claims, 4 Drawing Sheets
Specification includes a Sequence Listing.

```
                        SEQUENCE LISTING

<160> NUMBER OF SEQ ID NOS: 34

<210> SEQ ID NO 1
<211> LENGTH: 445
<212> TYPE: PRT
<213> ORGANISM: Artificial Sequence
<220> FEATURE:
<223> OTHER INFORMATION: Synthesized

<400> SEQUENCE: 1

Met Ile Glu Ser Val Glu Ser Phe Leu Ala Arg Leu Lys Lys Arg Asp
1               5                   10                  15

Pro Asp Gln Pro Glu Phe His Gln Ala Val Glu Val Leu Arg Ser
            20                  25                  30

Leu Trp Pro Phe Leu Glu Ala Asn Pro His Tyr Leu Thr Ser Gly Ile
            35                  40                  45

Leu Glu Arg Ile Cys Glu Pro Glu Arg Ala Val Val Phe Arg Val Ser
    50                  55                  60

Trp Val Asp Asp His Gly Lys Val Gln Val Asn Arg Gly Phe Arg Ile
65                  70                  75                  80

Gln Met Asn Ser Ala Ile Gly Pro Tyr Lys Gly Gly Leu Arg Phe His
                85                  90                  95

Pro Ser Val Asn Leu Gly Val Leu Lys Phe Leu Ala Phe Glu Gln Thr
            100                 105                 110

Phe Lys Asn Ser Leu Thr Ser Leu Pro Met Gly Gly Gly Lys Gly Gly
        115                 120                 125

Ser Asp Phe Asp Pro Lys Gly Lys Ser Asp Ala Glu Val Met Arg Phe
130                 135                 140

Cys Gln Ala Phe Met Ser Glu Leu Tyr Arg His Ile Gly Ala Asp Val
145                 150                 155                 160

Asp Val Pro Gly Gly Asp Ile Gly Val Gly Ala Arg Glu Ile Gly Phe
                165                 170                 175

Leu Phe Gly Gln Tyr Lys Arg Leu Ser Asn Gln Phe Thr Ser Val Leu
            180                 185                 190

Thr Gly Lys Gly Pro Ser Tyr Gly Gly Ser Leu Ile Lys Pro Glu Ala
        195                 200                 205

Thr Gly Phe Gly Cys Val Tyr Phe Ala Glu Glu Met Leu Lys Arg Arg
    210                 215                 220

Gly Glu Thr Val Glu Gly Lys Arg Val Ala Ile Ser Gly Ser Gly Asn
225                 230                 235                 240

Val Ala Gln Tyr Ala Ala Arg Lys Val Met Asp Leu Gly Gly Lys Val
                245                 250                 255

Ile Ser Leu Ser Asp Ser Glu Gly Thr Leu Tyr Cys Glu Ser Gly Leu
            260                 265                 270

Thr Glu Ala Gln Trp Gln Ala Val Leu Glu Leu Lys Asn Val Gln Arg
        275                 280                 285

Gly Arg Ile Ser Glu Leu Ala Ala Arg Phe Gly Leu Glu Phe Arg Ala
    290                 295                 300

Gly Gln His Pro Trp Gly Leu Ser Cys Asp Ile Ala Leu Pro Cys Ala
305                 310                 315                 320

Thr Gln Asn Glu Leu Asp Ala Glu Ala Ala Arg Ala Leu Leu Arg Asn
                325                 330                 335
```

```
Gly Cys Ile Cys Val Ala Glu Gly Ala Asn Met Pro Thr Thr Leu Glu
            340                 345                 350

Ala Val Asp Leu Phe Ile Glu Ala Gly Ile Leu Phe Ala Pro Gly Lys
            355                 360                 365

Ala Ser Asn Ala Gly Gly Val Ala Val Ser Gly Leu Glu Met Ser Gln
370                 375                 380

Asn Ala Met Arg Leu Leu Trp Thr Gly Gly Glu Val Asp Ser Lys Leu
385                 390                 395                 400

His Ala Ile Met Gln Ser Ile His His Ala Cys Val His Tyr Gly Glu
                405                 410                 415

Glu Asn Gly Gln Val Asn Tyr Val Lys Gly Ala Asn Ile Ala Gly Phe
            420                 425                 430

Val Lys Val Ala Asp Ala Met Leu Ala Gln Gly Val Val
            435                 440                 445
```

<210> SEQ ID NO 2
<211> LENGTH: 1338
<212> TYPE: DNA
<213> ORGANISM: Artificial Sequence
<220> FEATURE:
<223> OTHER INFORMATION: Synthesized

<400> SEQUENCE: 2

```
atgattgaga gcgtcgagtc tttcttggcc cgccttaaaa agcgcgaccc tgaccagccg    60
gagtttcatc aggcagttga ggaagtctta cgctcattat ggccgttcct ggaagctaac   120
ccccattatt tgactagcgg cattcttgaa cgtatttgcg agccggaacg tgccgtcgtt   180
ttccgtgtga gctgggtaga cgaccatgga aaggtgcaag tgaaccgtgg cttccgcatc   240
cagatgaact cagctatcgg cccatataaa ggcgggttgc gttttcatcc aagcgttaat   300
ttgggtgtct taaaattctt agcgttcgag caaacattta aaaacagctt aacatcgtta   360
cccatgggtg gaggaaaggg tggtagtgac ttcgacccaa aggggaagag cgatgcggaa   420
gtcatgcgtt tctgccaggc attcatgtca gagctttacc gtcacatcgg ggcggacgtc   480
gatgtgccag gggagatat tggcgtgggt gcgcgcgaga ttggattttt attcggtcag   540
tataagcgtc tgtctaacca gttcacctcg gtacttacgg gtaagggacc gtcatatggc   600
ggcagtttga ttaagccaga agctaccgga ttttggttgtg tttatttgc gaagaaatg    660
cttaagcgcc gtggagaaac cgtggaaggc aagcgtgttg ccattagtgg ctctgggaac   720
gtagcgcagt atgcggcccg caaggtgatg gatcttggcg aaaagtcat ttctttatca    780
gacagcgagg gcacattata ctgcgaatcc ggtttgactg aagctcaatg gcaagcagtg   840
ttggaactga gaatgtaca acgtggccgt atttcagaat tagccgcacg ctttggtctt    900
gaatttcgag cgggccaaca cccctggggt ttatcttgcg atatcgccct tccttgcgcg   960
acgcagaacg agcttgacgc cgaagctgcg cgtgctttac ttcgtaatgg atgcatctgc  1020
gtcgctgaag gggcgaacat gccgacaacc cttgaggcgg ttgatctgtt atcgaagcg   1080
ggtattctgt tcgctccagg taaagcctcg aatgctggcg gggttgcagt gtcgggttta  1140
gagatgtcgc aaaacgcaat gcgtttattg tggacagggg gcgaggttga ctcaaaattg  1200
catgctatca tgcagagcat ccatcatgct tgcgtacatt acggtgaaga gaacggtcag  1260
gtaaactacg taaggggggc gaatattgct ggattcgtga aggttgctga tgcaatgctg  1320
gcacaggggg tcgtctaa                                                1338
```

<210> SEQ ID NO 3
<211> LENGTH: 1197
<212> TYPE: DNA
<213> ORGANISM: Artificial Sequence
<220> FEATURE:
<223> OTHER INFORMATION: Synthesized

<400> SEQUENCE: 3

```
atgaccaaag ttctggccgt gctgtatccg gatccggtgg atggttttcc gccgaaatat      60
gttcgtgatg atattccgaa aatcacccat tatccggatg cagtaccgt tccgaccccg      120
gaaggcattg attttaaacc gggtgaactg ctgggtagcg ttagtggcgg tctgggcctg     180
aaaaaatatc tggaaagtaa aggtgtggaa tttgttgtta ccagtgataa agaaggcccg     240
gatagtgtgt ttgaaaaaga actgccgacc gccgatgtgg ttattagtca gccgttttgg     300
ccggcctatc tgaccgcaga tctgattgat aaagcaaaaa agctgaaact ggcaattacc     360
gccggtattg gcagcgatca tgtggatctg aatgccgcca atgaacataa tattaccgtt     420
gcagaagtga cctatagcaa tagtgttagt gttgcagaag cagaagtgat gcagctgctg     480
gccctggtgc gtaattttat tccggcacat gatattgtga agccggtgg ctggaatatt      540
gcagatgcag ttagccgtgc ctatgatctg aaggtatga ccgttggtgt gattggtgca      600
ggccgcattg gtcgtgccgt tctggaacgt ctgaaaccgt ttggcgttaa actggtgtat     660
aatcagcgcc aacagctgcc ggatgaagtt gaaaatgaac tgggcctgac ctatttttccg   720
gatgttcatg aaatggtgaa agttgtggat gccgttgttc tggcagcacc gctgcatgca    780
cagacctatc atctgtttaa tgatgaagtt ctggccacca tgaaacgtgg cgcctatatt     840
gtgaataata gccgcggcga agaagttgat cgcgatgcaa ttgttcgcgc actgaatagc     900
ggtcagattg gcggttatag tggcgatgtt tggtatccgc agccggcacc gaaagatcat     960
ccgtggcgta ccatgccgaa tgaagcaatg accccgcata tgagtggcac caccctgagt   1020
gcccaggcac gctatgccgc aggtgcacgt gaaattctgg aagatttct ggaagataaa     1080
ccgattcgtc cggaatatct gattgcccag ggtggtagtc tggccggtac cggtgccaaa   1140
agttataccg tgaaaaaagg cgaagaaacc ccgggtagcg gcgaagcaga aaaataa      1197
```

<210> SEQ ID NO 4
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (13)..(14)
<223> OTHER INFORMATION: n is a, c, g, or t

<400> SEQUENCE: 4
ggcagtttga ttnnkccaga agctacc      27

<210> SEQ ID NO 5
<211> LENGTH: 27
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (14)..(15)
<223> OTHER INFORMATION: n is a, c, g, or t

<400> SEQUENCE: 5
ggtagcttct ggmnnaatca aactgcc            27

<210> SEQ ID NO 6
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (13)..(14)
<223> OTHER INFORMATION: n is a, c, g, or t

<400> SEQUENCE: 6
gtcgatgtgc cannkggaga tattggcg            28

<210> SEQ ID NO 7
<211> LENGTH: 28
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (16)..(17)
<223> OTHER INFORMATION: n is a, c, g, or t

<400> SEQUENCE: 7
acgccaatat ctccmnntgg cacatcga            28

<210> SEQ ID NO 8
<211> LENGTH: 32
<212> TYPE: DNA
<213> ORGANISM: Artificial Sequence
<220> FEATURE:
<223> OTHER INFORMATION: Synthesized

<400> SEQUENCE: 8
tataattcat atacatccat gggttataat tc            32

<210> SEQ ID NO 9
<211> LENGTH: 32
<212> TYPE: DNA
<213> ORGANISM: Artificial Sequence
<220> FEATURE:
<223> OTHER INFORMATION: Synthesized

<400> SEQUENCE: 9
gaattataac ccatggatgt atatgaatta ta            32

<210> SEQ ID NO 10
<211> LENGTH: 30
<212> TYPE: DNA
<213> ORGANISM: Artificial Sequence
<220> FEATURE:
<223> OTHER INFORMATION: Synthesized

<400> SEQUENCE: 10
tataattcat atacatatgg gttataattc            30

<210> SEQ ID NO 11
<211> LENGTH: 30
<212> TYPE: DNA
<213> ORGANISM: Artificial Sequence
<220> FEATURE:
<223> OTHER INFORMATION: Synthesized

<400> SEQUENCE: 11
gaattataac ccatatgtat atgaattata                                    30

<210> SEQ ID NO 12
<211> LENGTH: 28
<212> TYPE: DNA
<213> ORGANISM: Artificial Sequence
<220> FEATURE:
<223> OTHER INFORMATION: Synthesized

<400> SEQUENCE: 12
tataattcat atacatgggt tataattc                                      28

<210> SEQ ID NO 13
<211> LENGTH: 28
<212> TYPE: DNA
<213> ORGANISM: Artificial Sequence
<220> FEATURE:
<223> OTHER INFORMATION: Synthesized

<400> SEQUENCE: 13
gaattataac ccatgtatat gaattata                                      28

<210> SEQ ID NO 14
<211> LENGTH: 26
<212> TYPE: DNA
<213> ORGANISM: Artificial Sequence
<220> FEATURE:
<223> OTHER INFORMATION: Synthesized

<400> SEQUENCE: 14
tataattcat atatgggtta taattc                                        26

<210> SEQ ID NO 15
<211> LENGTH: 26
<212> TYPE: DNA
<213> ORGANISM: Artificial Sequence
<220> FEATURE:
<223> OTHER INFORMATION: Synthesized

<400> SEQUENCE: 15
gaattataac ccatatga attata                                          26

<210> SEQ ID NO 16
<211> LENGTH: 14
<212> TYPE: DNA
<213> ORGANISM: Artificial Sequence
<220> FEATURE:
<223> OTHER INFORMATION: Synthesized

<400> SEQUENCE: 16
atatacatcc agat                                                     14

<210> SEQ ID NO 17
<211> LENGTH: 13
<212> TYPE: DNA
<213> ORGANISM: Artificial Sequence
<220> FEATURE:
<223> OTHER INFORMATION: Synthesized

<400> SEQUENCE: 17
atatacatcc aga                                                      13

<210> SEQ ID NO 18
<211> LENGTH: 10
<212> TYPE: DNA

```
<213> ORGANISM: Artificial Sequence
<220> FEATURE:
<223> OTHER INFORMATION: Synthesized

<400> SEQUENCE: 18
atatacatcc                                                                10

<210> SEQ ID NO 19
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (19)..(20)
<223> OTHER INFORMATION: n is a, c, g, or t

<400> SEQUENCE: 19
gaagtgacct atagcaatnn kgttagtgtt gc                                       32

<210> SEQ ID NO 20
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(22)
<223> OTHER INFORMATION: n is a, c, g, or t

<400> SEQUENCE: 20
ctgcttctgc aacactaacm nnattgctat ag                                       32

<210> SEQ ID NO 21
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(21)
<223> OTHER INFORMATION: n is a, c, g, or t

<400> SEQUENCE: 21
cgttaaactg gtgtataatn nkcgccatca gc                                       32

<210> SEQ ID NO 22
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (18)..(19)
<223> OTHER INFORMATION: n is a, c, g, or t

<400> SEQUENCE: 22
ccggcagctg atggcgmnna ttatacacc                                           29

<210> SEQ ID NO 23
<211> LENGTH: 30
<212> TYPE: DNA
<213> ORGANISM: Artificial Sequence
<220> FEATURE:
<223> OTHER INFORMATION: Synthesized
```

```
<220> FEATURE:
<221> NAME/KEY: misc_feature
<222> LOCATION: (16)..(17)
<223> OTHER INFORMATION: n is a, c, g, or t

<400> SEQUENCE: 23
ctggtgtata atcagnnkca tcagctgccg                                     30

<210> SEQ ID NO 24
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(22)
<223> OTHER INFORMATION: n is a, c, g, or t

<400> SEQUENCE: 24
cttcatccgg cagctgatgm nnctgattat ac                                  32

<210> SEQ ID NO 25
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (17)..(18)
<223> OTHER INFORMATION: n is a, c, g, or t

<400> SEQUENCE: 25
ggtgtataat cagcgcnnkc agctgccgg                                      29

<210> SEQ ID NO 26
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(22)
<223> OTHER INFORMATION: n is a, c, g, or t

<400> SEQUENCE: 26
caacttcatc cggcagctgm nngcgctgat ta                                  32

<210> SEQ ID NO 27
<211> LENGTH: 30
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (19)..(20)
<223> OTHER INFORMATION: n is a, c, g, or t

<400> SEQUENCE: 27
gaagcaatga ccccgcatnn kagtggcacc                                     30

<210> SEQ ID NO 28
<211> LENGTH: 30
<212> TYPE: DNA
<213> ORGANISM: Artificial Sequence
<220> FEATURE:
```

<223> OTHER INFORMATION: Synthesized
<220> FEATURE:
<221> NAME/KEY: misc_feature
<222> LOCATION: (19)..(20)
<223> OTHER INFORMATION: n is a, c, g, or t

<400> SEQUENCE: 28
ctcagggtgg tgccactmnn atgcggggtc                            30

<210> SEQ ID NO 29
<211> LENGTH: 31
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(21)
<223> OTHER INFORMATION: n is a, c, g, or t

<400> SEQUENCE: 29
cccgcatatg agtggcaccn nkctgagtgc c                          31

<210> SEQ ID NO 30
<211> LENGTH: 31
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (20)..(21)
<223> OTHER INFORMATION: n is a, c, g, or t

<400> SEQUENCE: 30
gcgtgcctgg gcactcagmn nggtgccact c                          31

<210> SEQ ID NO 31
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (17)..(18)
<223> OTHER INFORMATION: n is a, c, g, or t

<400> SEQUENCE: 31
ggccggtacc ggtgccnnka gttataccg                             29

<210> SEQ ID NO 32
<211> LENGTH: 31
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (22)..(23)
<223> OTHER INFORMATION: n is a, c, g, or t

<400> SEQUENCE: 32 cctttttca cggtataact mnnggcaccg g                           31

<210> SEQ ID NO 33
<211> LENGTH: 30
<212> TYPE: DNA
<213> ORGANISM: Artificial Sequence

```
<220> FEATURE:
<223> OTHER INFORMATION: Synthesized
<220> FEATURE:
<221> NAME/KEY: misc_feature
<222> LOCATION: (17)..(18)
<223> OTHER INFORMATION: n is a, c, g, or t

<400> SEQUENCE: 33
cggtgccaaa agttatnnkg tgaaaaaagg                                    30

<210> SEQ ID NO 34
<211> LENGTH: 32
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (23)..(24)
<223> OTHER INFORMATION: n is a, c, g, or t

<400> SEQUENCE: 34
ggtttcttcg cctttttttca cmnnataact tt                                 32
```

PHOSPHINOTHRICIN DEHYDROGENASE MUTANT, GENETICALLY ENGINEERED BACTERIUM AND ONE-POT MULTI-ENZYME SYNCHRONOUS DIRECTED EVOLUTION METHOD

This is a U.S. national stage application of PCT Application No. PCT/CN2020/139770 under 35 U.S.C. 371, filed Dec. 26, 2020 in Chinese, claiming priority to Chinese Patent Applications No. 202010614951.3, filed Jun. 30, 2020, all of which are hereby incorporated by reference.

Applicant hereby electronically submits the Sequence Listing in ASCII text file (CRF format) with the file name of P76184USO_SEQ_LIST_ST25.txt, created on Oct. 15, 2021 and with the size of 16,384 bytes, which is hereby incorporated by reference. It is respectfully submitted that the Sequence Listing in CRF format does not include new matter. In addition, the Sequence Listings hereby submitted satisfy both the paper copy requirement under 37 CFR 1.821 (c) and the computer-readable form requirement of 37 CFR 1.182 (e). Thus, the requirement of 37 CFR 1.821 (f) has been satisfied.

FIELD OF TECHNOLOGY

The present invention relates to the field of biochemical technology, in particular to a phosphinothricin dehydrogenase mutant, a recombinant bacterium and a one-pot multi-enzyme synchronous directed evolution method.

BACKGROUND

Phosphinothricin (also known as glufosinate, PPT for short), with a chemical name of 2-amino-4-[hydroxy (methyl)phosphono]-butyric acid, is the second largest herbicide tolerated by transgenic crops in the world. It was first developed and produced by Hoechst (which is now owned by Bayer after several mergers) and also known as glufosinate ammonium salt, Basta and Buster. Phosphinothricin belongs to phosphonic acid herbicides and non-selective contact herbicides and is a glutamine synthetase inhibitor.

Phosphinothricin has two optical isomers, L-phosphinothricin and D-phosphinothricin. However, only the L-form has physiological activity, and is easily decomposed in the soil, less toxic to humans and animals, wide in herbicidal spectrum and less destructive to the environment.

Phosphinothricin currently available on the market is generally a racemic mixture. If the phosphinothricin product can be used as a pure optical isomer in the L-configuration, the consumption of phosphinothricin can be remarkably reduced, which is of great significance for improving atomic economy, reducing use cost and lowering environmental pressure.

There are three main methods for preparing chiral pure L-phosphinothricin: chiral resolution, chemical synthesis and biocatalysis. The biocatalysis method for producing phosphinothricin has the advantages of strict stereoselectivity, mild reaction conditions, and high yield, and is an advantageous method for producing L-phosphinothricin, which mainly includes the following three categories:

1) L-phosphinothricin is obtained by direct hydrolysis of L-phosphinothricin derivatives as the substrate through an enzyme method. For this route, the main advantages are that the conversion is high, and the e.e. value of the product is high, but expensive and difficult-to-obtain chiral raw materials are needed as precursors, resulting in increased cost, which is not conductive to industrialized production. For example, the simplest process for preparing L-phosphinothricin by the biological method is to directly hydrolyze bialaphos by using protease. Bialaphos is a natural tripeptide compound, which, under the catalysis of protease, can lose two molecules of L-alanine to obtain L-phosphinothricin.

2) L-phosphinothricin is obtained through selective resolution of a precursor of racemic phosphinothricin by an enzyme. The main advantages are that the raw materials are relatively easily available, and the catalyst activity is high, but the theoretical yield can only reach 50%, resulting in the waste of raw materials. For example, Cao et al. (Cao C-H, Cheng F, Xue Y-P, Zheng Y-G (2020) Efficient synthesis of L-phosphinothricin using a novel aminoacylase mined from Stenotrophomonas maltophilia. Enzyme and Microbial Technology 135 doi:10.1016/j.enzmictec.2019.109493) performed chiral resolution of N-acetyl-PPT using a novel aminoacylase derived from Stenotrophomonas maltophilia to obtain L-phosphinothricin. Whole cells were used for catalysis, the conversion was >49% in 4 hours and optically pure L-PPT (>99.9% e.e.) was obtained.

3) With α-keto acid-2-carbonyl-4-(hydroxymethylphosphono)butyric acid (PPO) as the substrate, L-phosphinothricin is obtained by asymmetric synthesis with enzymes, mainly including transaminase and phosphinothricin dehydrogenase. Bartsch et al. (Bartsch K (2005) Process for the preparation of 1-phosphinothrcine by enzymatic transamination with aspartate. U.S. Pat. No. 6,936,444B1) used PPO as the substrate, L-aspartic acid as the amino donor to react as catalyzed by transaminase that was screened and separated from soil microorganisms and has specific enzymatic activity for PPO and L-aspartic acid. With a substrate concentration of 552 mM, the reaction was carried out at a very high temperature (80° C.) for 4 hours, and the conversion reached 52%, and the space-time yield was 4.5 g L-PPT/g of biocatalyst/hour. However, preparation of L-phosphinothricin using transaminase has two major defects. One is that this is a reversible reaction, the raw material PPO cannot be completely converted into L-PPT, and it is impossible for the conversion to reach 100%; second, to make the reversible reaction proceed in the direction of producing L-PPT, at least 2 times of L-aspartic acid as the amino donor is needed, whereas excessive aspartic acid brings great trouble to the separation of L-PPT.

Among various enzymatic synthesis routes of phosphinothricin, the ketocarbonyl group in the keto acid intermediate is a latent chiral functional group, with which a chiral center can be constructed through an enzymatic synthesis route; and the keto acid route becomes a route suitable for industrial development and production of L-phosphinothricin because the raw materials are cheap and readily available, and the use of highly toxic cyanides can be avoided.

Amino acid dehydrogenase (EC 1.4.1.X, AADH) is a kind of amino acid dehydrogenase that can achieve reversible deamination of amino acids to produce the corresponding keto acids, which requires the participation of nucleoside coenzyme (NAD(P)$^+$) in the reaction. It has been widely used in the synthesis of natural and non-natural a-amino acids. According to their substrate specificity, amino acid dehydrogenases can be divided into glutamate dehydrogenase, leucine dehydrogenase, alanine dehydrogenase, and valine dehydrogenase or the like. An amino acid dehydrogenase will be called "phosphinothricin dehydrogenase (PPTDH)" if it shows activity towards phosphinothricin precursors.

Glucose dehydrogenase (EC1.1.1.47, GDH) is an important enzyme for the regeneration of coenzyme NAD(P)H in the redox catalytic reaction.

SUMMARY OF THE INVENTION

The present invention provides a one-pot multi-enzyme synchronous directed evolution method, which can realize the synchronous directed evolution of the gene elements of and between a phosphinothricin dehydrogenase and a glucose dehydrogenase or formate dehydrogenase. The present invention provides a phosphinothricin dehydrogenase mutant, a high expressed glucose dehydrogenase or formate dehydrogenase mutant, an engineered bacterium containing the genes of the two enzymes, and an application thereof in preparing L-phosphinothricin. The two enzymes in the recombinant bacterium undergo one-pot multi-enzyme synchronous evolution, so that the synergistic efficiency of the two enzymes in the process of synthesizing L-PPT is higher; and in the catalytic preparation of L-phosphinothricin, the substrate conversion, the space-time yield, and the total turnover number are high. Also, the reaction process is further shortened.

The present invention provides a phosphinothricin dehydrogenase mutant, which is obtained by mutating alanine at position 164 to glycine, arginine at position 205 to lysine, and threonine at position 332 to alanine in a phosphinothricin dehydrogenase derived from *Pseudomonas fluorescens*, wherein the phosphinothricin dehydrogenase mutant has an amino acid sequence as shown in SEQ ID No.1.

The present invention also provides a gene encoding the phosphinothricin dehydrogenase mutant.

The present invention also provides a recombinant bacterium comprising a host cell and a target gene transformed into the host cell, wherein the target gene comprises the gene.

The recombinant bacterium, wherein the target gene further comprises a gene encoding a glucose dehydrogenase or a gene encoding a formate dehydrogenase.

The recombinant bacterium, wherein a double gene expression vector is used, the gene of the phosphinothricin dehydrogenase mutant is cloned into a first polyclonal site region thereof, and the gene encoding the glucose dehydrogenase or the gene encoding the formate dehydrogenase is cloned into a second polyclonal site region thereof.

The sequence of the gene encoding the glucose dehydrogenase has a GenBank accession number of KM817194.1, and the length of linking bases between an initiation codon of the gene encoding the glucose dehydrogenase and the corresponding ribosome binding site on a plasmid is 8-10 bp. Specifically, the best effect is achieved when the length of the linking bases is 8 bp.

The gene encoding the formate dehydrogenase has a sequence as shown in SEQ ID No.3. The formate dehydrogenase encoded by the gene sequence as shown in SEQ ID No.3 is obtained by mutating histidine at position 224 of a formate dehydrogenase derived from *Lactobacillus buchneri* to glutamine.

The present invention also provides an application of the phosphinothricin dehydrogenase mutant, the gene or the recombinant bacterium in preparing L-phosphinothricin.

The present invention provides a method for preparing L-phosphinothricin, wherein 2-carbonyl-4-(hydroxymethylphosphinic)butyric acid as a substrate and glucose or ammonium formate as a co-substrate react as catalyzed by a catalyst in the presence of an inorganic amino donor and a coenzyme circulation system to obtain L-phosphinothricin;

The coenzyme circulate system is a glucose dehydrogenase circulation system or a formate dehydrogenase circulate system; the catalyst is the recombinant bacterium, a crude enzyme liquid of the recombinant bacterium, or the immobilized recombinant bacterium;

When the recombinant bacterium contains the gene encoding the glucose dehydrogenase, the co-substrate is glucose, and the coenzyme circulation system is the glucose dehydrogenase circulation system; and when the recombinant bacterium contains the gene encoding the formate dehydrogenase, the co-substrate is ammonium formate, and the coenzyme circulation system is the formate dehydrogenase circulation system. The inorganic amino donor is ammonium sulfate in the glucose dehydrogenase circulation system and ammonium formate in the formate dehydrogenase circulation system.

The present invention also provides a one-pot multi-enzyme synchronous directed evolution method, which comprises steps of:

(1) cloning the gene of a regeneration enzyme used in the coenzyme circulation system into a double gene expression vector for co-expression with phosphinothricin dehydrogenase; (2) constructing an error-prone PCR library for the coupled co-expressed double enzymes by the error-prone PCR method and cloning them into the double gene expression vector; (3) introducing the expression vector cloned with the double genes into a host cell to culture, carrying out L-phosphinothricin preparation experiments on the obtained single colonies separately and screening a strain with improved preparation efficiency; and (4) determining the mutation site of the phosphinothricin dehydrogenase gene in the screened strain, carrying out site-saturation mutagenesis on the gene, and screening to obtain a mutant with the highest activity.

In the present application, the gene of phosphinothricin dehydrogenase derived from *Pseudomonas fluorescens* and with an NCBI accession number of WP_150701510.1, the gene of the glucose dehydrogenase derived from *Exiguobacterium sibiricum* and with a GenBank No. of ACB59697.1, and the gene of the formate dehydrogenase derived from *Lactobacillus buchneri* and with an NCBI accession number of WP_013726924.1 are cloned. The phosphinothricin dehydrogenase gene is introduce into MCS1 (polyclonal site 1) on pETDuet-1 plasmid, the glucose dehydrogenase or formate dehydrogenase gene is introduced into MCS2 (polyclonal site 2) on pETDuet-1 plasmid vector with the phosphinothricin dehydrogenase. The pETDuet-1 plasmid is then transformed into *Escherichia coli* to achieve heterologous expression of the gene. The phosphinothricin dehydrogenase is able to catalyze the asymmetric reductive amination of PPO into L-PPT, while the coenzyme NADPH turns into NADP$^+$. Glucose dehydrogenase is capable of catalyzing glucose to generate gluconic acid, or formate dehydrogenase is capable of catalyzing ammonium formate to generate ammonium ions, carbon dioxide and water while changing NADP$^+$ into NADPH, thereby forming coenzyme circulation in cells (FIG. 4). Although the phosphinothricin dehydrogenase mutant A164G_R205K_T332A shows obviously improved activity towards PPO, in the preparation of L-PPT by the one-pot method using the phosphinothricin dehydrogenase mutant coupled with the glucose dehydrogenase or the formate dehydrogenase, the overall enzymatic activity of the two enzymes is still to be improved. Therefore, it is desirable to catalyze the production of L-PPT through one-pot synchronous directed evolution of the phosphinothricin dehydrogenase and the glucose dehydrogenase or the formate dehydrogenase. This method is novel and is of high value in industrial application.

Compared with the prior art, the present invention has the following beneficial effects:

(1) The present invention develops a one-pot multi-enzyme synchronous directed evolution technology, where the obtained PPTDH-A164G_R205K_T332A and EsGDH are coupled and co-expressed, and the length of bases between the ribosome binding site and an EsGDH coding gene initiation codon is optimized at the same time, so that the EsGDH is further overexpressed, or LbFDH is mutated to obtain the mutant LbFDH-H224Q, thereby further improving the conversion and the space-time yield in one-pot L-PPT biosynthesis. After one-pot multi-enzyme synchronous directed evolution, the total turnover number is increased by 5.8 times as compared with that of the previous enzyme mutant PPTDH-A164G_R205K_T332A alone, the final space-time yield of L-PPT reaches $7110 \ g \cdot L^{-1} \cdot d^{-1}$, and the e.e. value of the product L-PPT is greater than 99%.

(2) The method for preparing L-PPT provided by the present invention features high conversion of raw materials, high yield and easy separation and purification of the product.

(3) Compared with the chemical method and other biological methods (such as transaminase method), the method for preparing L-PPT provided by the present invention has the advantages of relatively simple process, high raw material conversion of up to 100%, and high product optical purity (e.e. >99%).

DETAILED DESCRIPTION OF THE EMBODIMENTS

The experimental methods in the present invention are conventional methods unless otherwise specified, and the operation of gene cloning can be specifically found in the Molecular Cloning: A Laboratory Manual edited by J. Sambrook et al.

Reagents used for upstream genetic engineering operations: the one-step cloning kits used in the examples of the present invention were all purchased from Vazyme Biotech Co. Ltd. (Nanjing); the plasmid extraction kits and DNA recovery and purification kits were purchased from Axygen Biotechnology (Hangzhou) Limited; the plasmids were purchased from Sangon Biotech (Shanghai); the DNA marker, Fast Pfu DNA polymerase, low molecular weight protein markers, agarose electrophoresis reagents, primer synthesis and gene sequencing, and gene synthesis were carried out by Hangzhou TSINGKE Biological Technology Co., Ltd. For the use methods of the above reagent, please refer to their respective instructions.

Reagents used in the downstream catalytic process: 2-carbonyl-4-(hydroxymethylphosphono)butyric acid (PPO), D,L-PPT and L-PPT standards were purchased from Sigma-Aldrich; NADPH was purchased from Bontac Bio-engineering (Shenzhen) Co., Ltd; other commonly used reagents were purchased from Sinopharm Chemical Reagent Co., Ltd.

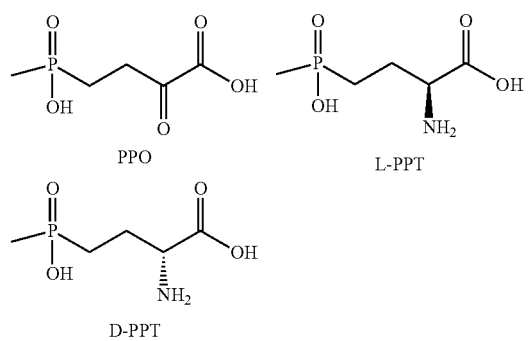

Figure 1:
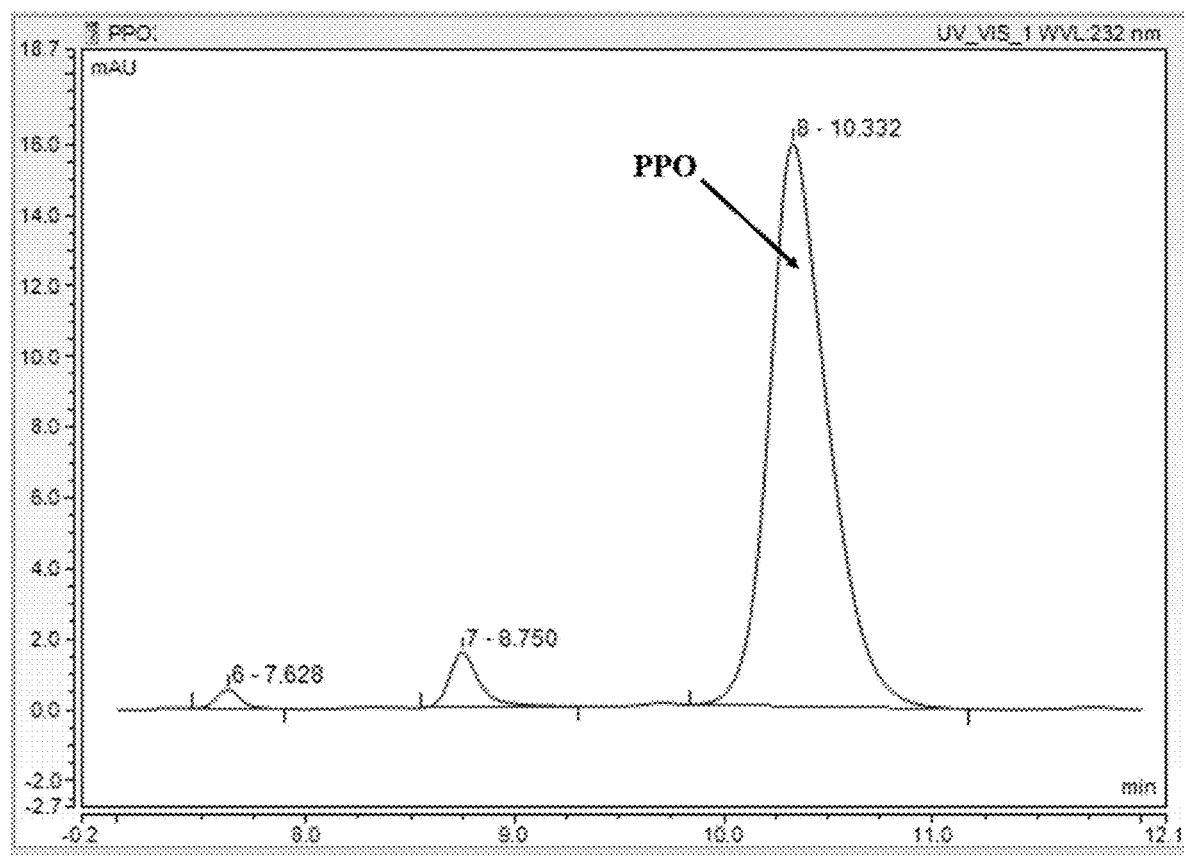
FIG. 1 is a high-performance liquid chromatography (HPLC) chromatogram of a PPO sample.

The high-performance liquid chromatography detection method in the following examples is as follows:

The substrate PPO concentration was detected by high performance liquid chromatography (HPLC) as follows: Column model: QS-C18 column, 5 μm, 4.6×250 mm. For the mobile phase: 50 mM ammonium dihydrogen phosphate was dissolved in 800 mL of ultra-pure water, 10 mL of tetrabutyl ammonium hydroxide (10%) was added thereto, diluted to 1000 mL with water, adjusted to pH 3.8 with phosphoric acid, and mixed with acetonitrile in a volume ratio of 88:12. The detection wavelength: 232 nm; flow rate: 1.0 mL/min; column temperature: 40° C.; and retention time of 2-carbonyl-4-(hydroxymethylphosphinyl)-butyric acid (PPO): 10.3 min (FIG. 1).

Figure 2:
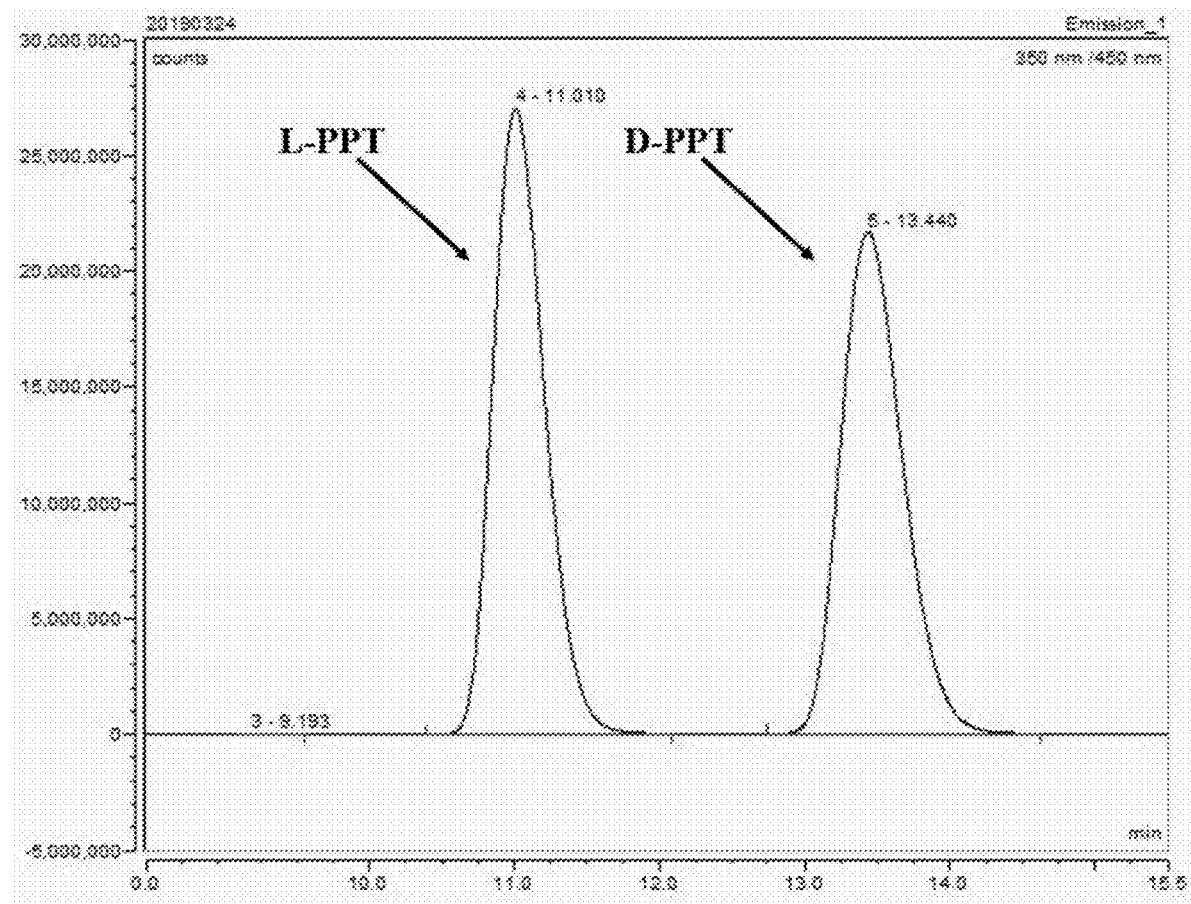
FIG. 2 is a high performance liquid chromatography (HPLC) chromatogram of a D,L-PPT sample.

Chiral analysis and concentration analysis of the products were conducted through pre-column derivatization high-performance liquid chromatography, which specifically comprises:

(1) Chromatographic conditions: column model: QS-C18, 5 μm, 4.6×250 mm; mobile phase: 50 mM ammonium acetate solution : methanol=10:1; fluorescence detection wavelength: $\lambda_{ex}$=340 nm, $\lambda_{em}$=455 nm; flow rate: 1 mL/min; column temperature: 30° C., L-PPT retention time: 11 min, and D-PPT retention time: 13.4 min (FIG. 2).

(2) Derivatization reagent: 0.1 g of o-phthalaldehyde and 0.12 g of N-acetyl-L-cysteine were weighed separately and dissolved in 10 mL of ethanol, 40 mL of 0.1 mol/L boric acid buffer (pH 9.8) was added and the mixture was shaken to fully dissolve and then stored in a refrigerator at 4° C. for later use (no more than 4 days).

(3) Derivatization reaction and HPLC detection: Ultrapure water was used to make up to 1 mL, i.e., the reaction mixture was diluted 10 times. The diluted sample was subjected to derivatization treatment. To 200 μL of the diluted reaction mixture, 400 μL of the derivatization reagent was added for derivatization at 30° C. for 5 min, and then 400 μL of ultra-pure water was added to make up to 1 mL. The mixture was centrifuged at 12000 rpm for 1 min. The supernatant was passed through a 0.22 μM microfiltration membrane as a liquid sample, and detected for PPO, L-PPT, D-PPT, and e.e. value by HPLC.

EXAMPLE 1

Figure 3:
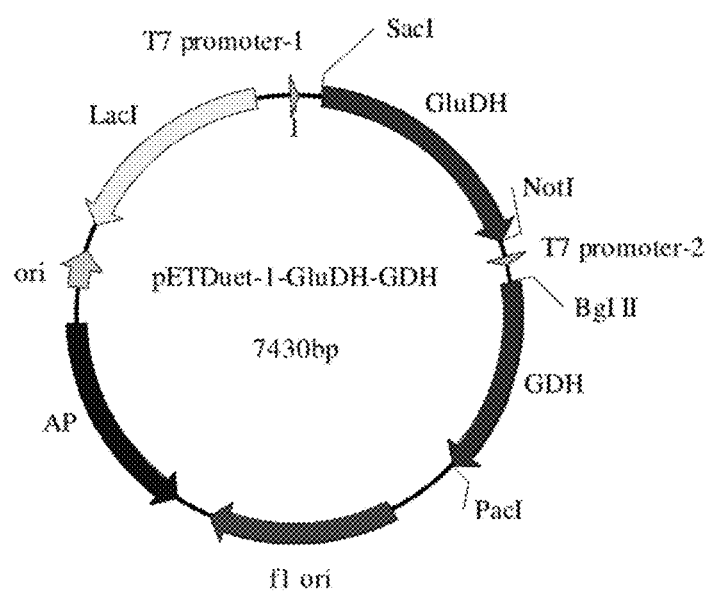
FIG. 3 is a plasmid profile of the expression vector with coupled PPTDH and EsGDH obtained in Example 1.
Figure 4:
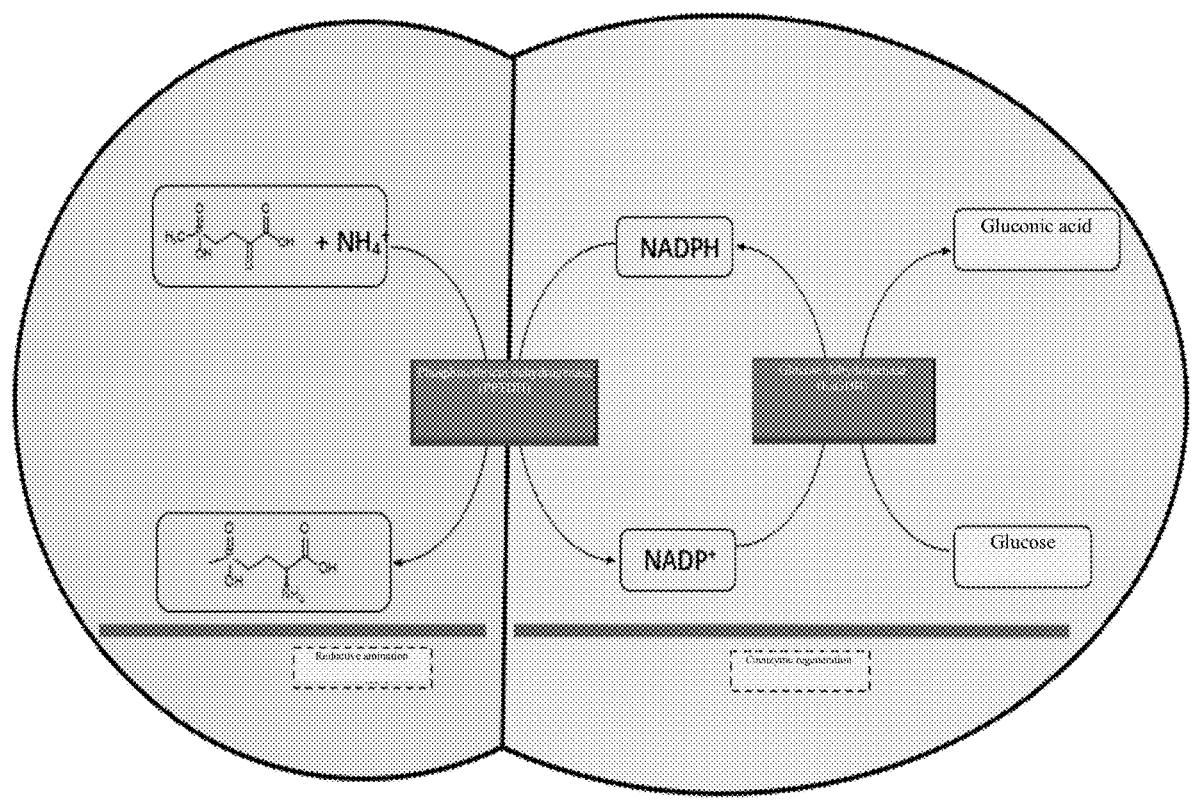
FIG. 4 is a schematic diagram of the reaction for preparing L-PPT through asymmetric reductive amination of PPO as catalyzed by coupled PPTDH and EsGDH double enzymes in Example 1.

Construction of Expression Vector and Engineered Bacterium with Coupled Phosphinothricin Dehydrogenase and Glucose Dehydrogenase or Formate Dehydrogenase Construction of expression vector: The synthesis work involving phosphinothricin dehydrogenase, glucose dehydrogenase and formate dehydrogenase genes described below was conducted by Hangzhou TSINGKE Biological Technology Co., Ltd. The phosphinothricin dehydrogenase gene (NCBI accession number: WP_150701510.1) derived from *Pseudomonas fluorescens* was seamlessly cloned between SacI and NotI at the first polyclonal site of the pETDuet-1 vector by PCR, and the glucose dehydrogenase gene (NCBI accession number: KM817194.1) derived from *Exiguobacterium sibiricum* or the formate dehydrogenase gene (NCBI accession number: WP_013726924.1) derived from *Lactobacillus buchneri* was seamlessly cloned between BglII and PacI at the second polyclonal site of the pETDuet-1 vector by PCR to obtain the expression vector pETDuet-PPTDH-EsGDH (FIG. 3) or pETDuet-PPTDH-LbFDH with phosphinothricin dehydrogenase. The PCR procedure was operated as follows: pre-denaturation at 95° C. for 3 minutes; denaturation at 95° C. for 15 seconds, annealing at 53-58° C. for 15 seconds and elongation at 72° C. for 1.5 minutes, 25 cycles in total; and then elongation at 72° C. for 10 minutes.

Preparation of competent cells: The *E.coli* BL21(DE3) strain preserved in a glycerol tube was obtained from a refrigerator at −80° C., streaked on an antibiotic-free LB plate to culture at 37° C. for 10 hours to obtain single colonies. The single colonies on the LB plate were picked, inoculated into a test tube containing 5 μL of LB culture medium to culture at 37° C. and 180 rpm for 9 hours. Then, 200 μL of the bacterial liquid was taken from the test tube and inoculated into 50 mL of LB culture medium to culture at 37° C. and 180 rpm until $OD_{600}$ reached 0.4-0.6. The bacterial liquid was pre-cooled on ice, put into a sterilized centrifuge tube, placed on ice for 10 minutes, and then centrifuged at 4° C. and 5,000 rpm for 10 minutes. The supernatant was poured out (contamination should be prevented), and the precipitated cells were re-suspended in pre-cooled 0.1 mol/L aqueous $CaCl_2$ solution and placed on ice for 30 minutes, and then centrifuged at 4° C. and 5,000 rpm for 10 minutes. The supernatant was discarded and the precipitated cells were re-suspended in pre-cooled 0.1 mol/L aqueous $CaCl_2$ solution containing 15% glycerol. A total of 100 μL of the re-suspended cells were aliquoted into a sterilized 1.5 mL centrifuge tube and stored in a refrigerator at −80° C. for later use.

Construction of engineered bacteria library: The competent cells of *E. coli* BL21(DE3) (Invitrogen) stored at −80° C. were placed in an ice bath at 0° C. for 10 minutes, and then 5 μL of the expression vector pETDUET-1-PPTDH with phosphinothricin dehydrogenase and glucose dehydrogenase was added thereto in a super clean bench, the mixture was placed in an ice bath at 0° C. for 30 minutes, heat-shocked at 42° C. for 90 seconds, placed in an ice bath at 0° C. for 2 minutes, 600 μL of LB culture medium was added thereto, and the mixture was then shaking-cultured at 37° C. and 200 rpm for 1 hour. The mixture was coated on an LB plate containing 50 μg/ml ampicillin resistance to culture at 37° C. for 8-12 hours, thereby obtaining a recombinant *E. coli* BL21(DE3)/pETDuet-1-PPTDH-EsGDH or pETDuet-PPTDH-LbFDH engineered bacterium containing the recombinant expression plasmid.

EXAMPLE 2

Construction and Screening of Coupled Phosphinothricin Dehydrogenase and Glucose Dehydrogenase/formate Dehydrogenase Double-enzyme Gene Library 1) Establishment of High-throughput Screening Method Preparation of 50 mL of working solution (derivatization reagent): 0.013 g of o-phthalaldehyde and 0.032 g of N-acetyl-L-cysteine were dissolved with a boric acid buffer with pH=9.8 to a constant volume of 50 mL, shaken to fully dissolve, and stored in a refrigerator at 4° C. for later use (no more than 4 days) as a high-throughput working solution, also known as derivatization reagent. Then, 50 μL of the sample reaction mixture was added into 50 μL of the working solution to react under shaking for 30 seconds, and then 100 μL of ddH2O was added. The fluorescence value was measured at $\lambda_{ex}$=340 nm and $\lambda_{em}$=455 nm.

2) One-pot Multi-enzyme Synchronous Directed Evolution

Comparative Example: PPTDH and EsGDH underwent directed evolution by using multi-enzyme stepwise directed evolution separately. After screening among 20,000 clones, no PPTDH (PfGluDH) and EsGDH with significantly increased viability were obtained. With wild-type lyophilized *E. coli* cells with PPTDH(PfGluDH) and EsGDH as the biocatalyst, the conversion of 100 mM PPO to L-PPT was 37.3% after 12 hours (without exogenous $NADP^+$). When the PPO concentration was increased to 300 mM and 500 mM, the conversion decreased to 11.5% and 7.7% respectively (without exogenous $NADP^+$), and the e.e. value reached more than 99%. Therefore, the efficiency of the multi-enzyme catalytic reaction for L-PPT synthesis needs to be improved.

According to the strategy adopted by the present invention, with the recombinant expression plasmid pETDuet-1-PPTDH-EsGDH obtained in Example 1 as the initial plasmid, error-prone PCR was performed on the gene expression regulation elements of and between phosphinothricin dehydrogenase and glucose dehydrogenase simultaneously to screen strains with improved activity. For the error-prone PCR, there were two rounds of PCR. In the first round of PCR, error-prone PCR was performed on the target gene and the concentration of $Mn^{2+}$ added was selected to be 0.15 mM; and in the second round of PCR, the product of the first round of error-prone PCR was cloned onto the expression vector pETDuet-1 using the megaprimer method to obtain a recombinant plasmid with the error-prone target gene (Miyazaki K, Takenouchi M. 2002.Creating Random Mutagenesis Libraries Using Megaprimer PCR of Whole Plasmid. BioTechniques 33:1033-1038.). The product of the second round of PCR digested by DpnI was transformed into *E. coli* BL21(DE3) for expression and screening.

Preparation of reaction mixture: The reaction mixture comprised the substrate PPO (2-carbonyl-4-(hydroxymethylphosphinic)butyric acid) with a final concentration of 300 mM, ammonium sulfate with a final concentration of 750 mM, glucose with a final concentration of 360 mM, and phosphate buff at pH=7.5 as the reaction medium.

After colonies came up on the plate, single colonies were picked from the plates and inoculated into a 96-well plate containing 1.0 mL of LB culture medium (containing 135 μM ampicillin) in each well. After incubation at 37° C. for 8 hours, 200 μL of the bacterial liquid was transferred to another 96-well plate containing 800 μL of LB culture medium (containing 135 μM ampicillin and 0.1 mM IPTG) and incubated at 22° C. and 200 rpm for 16 hours. The cultured bacterial liquid was centrifuged at 4,000 rpm for 10 minutes, the supernatant was discarded, and the bacterial cells were collected at the bottom of the well. Next, the catalytic reaction was verified. The reaction mixture was added into a 96-deep-well plate, 500 μL per well, and repeatedly blown with a pipette to re-suspend the cells collected from the 96-well plate. Then, the 96-deep-well plate was placed on a shaker at 40° C. and 200 rpm to react for 1 hour, and the supernatant was collected by centrifugation for high-throughput screening.

Primary screening: 50 μL of the sample reaction supernatant was pipetted and mixed with 50 μL of the working solution to react with shaking for 30 s. Then, 100 μL of ddH$_2$O was added thereto, and the mixture was measured for fluorescence value under the conditions of $\lambda_{ex}$=340 nm and $\lambda_{em}$=455 nm. Strains with higher fluorescence value than that of the wild-type pETDuet-1-PPTDH-EsGDH reaction mixture were screened, and the corresponding preserved strains were found and streak-cultured, and then high-concentration bacterial liquid and 30% glycerol in a ratio of 1:1 were pipetted and added into a glycerol tube, which was finally stored in a refrigerator at −80° C.

Through preliminary screening by the high-throughput screening method and the liquid-phase re-screening, more than 8,000 mutants were selected, and finally four mutants with improved activity were screened, which improved the yield of L-PPT by at least three times. Among others, three of the mutants were mutants A164G, R205K, and T332A derived from phosphinothricin dehydrogenase, and the fourth mutant was from the deletion of the bases between the second cloning site RBS and glucose dehydrogenase, resulting in increased activity. As analyzed, the reason is that the deletion of the bases results in enhanced expression of glucose dehydrogenase, thus improving the coenzyme circulation efficiency.

EXAMPLE 3

Site-saturation Mutagenesis of Phosphinothricin Dehydrogenase in Multi-enzyme Coupling Reaction System In order to further screen strains with potentially improved activity, the two beneficial mutation sites A164 and R205 of phosphinothricin dehydrogenase obtained in Example 2 were subjected to site-saturation mutagenesis for further screening, with the PCR primer design shown in Table 1. The PCR system (50 μL) was as follows: 25 μL of 2*Phanta Max buffer, 1 μL of dNTPs, 1 μL of each of the upper and lower primers for mutation, 1 μL of template (original strain), 0.5 μL of Pfu DNA polymerase, and ddH2O making up to 50 μL. The PCR conditions were as follows: pre-denaturation at 95° C. for 3 minutes; denaturation at 95° C. for 15 seconds, annealing at 60° C. for 15 seconds, and elongation at 72° C. for 7 minutes and 20 seconds, 30 cycles; final elongation at 72° C. for 10 minutes. The PCR product was verified by DNA agarose gel electrophoresis. After the template was digested with DpnI, the PCR product was transformed into *E. coli* BL21(DE3) competent cells, the transformed product was coated on an LB plate containing 50 μg/mL ampicillin resistance, and placed upside down to culture at 3° C. overnight. The dominant mutants were screened out from the obtained mutants, and were sent to Hangzhou TSINGKE Biological Technology Co., Ltd for sequencing confirmation, and stored.

TABLE 1

Phosphinothricin dehydrogenase site-saturation mutagenesis primer design

| Primer name | Primer sequence (5'-3') |
|---|---|
| PfGluDH-205-F | GGCAGTTTGATTNNKCCAGAAGCTACC |
| PfGluDH-205-R | GGTAGCTTCTGGMNNAATCAAACTGCC |
| PfGluDH-164-F | GTCGATGTGCCANNKGGAGATATTGGCG |
| PfGluDH-164-R | ACGCCAATATCTCCMNNTGGCACATCGA |

The high-throughput screening method and the reaction system for measuring enzyme activity are the same as in Example 2.

TABLE 2

Conversion of multi-enzyme catalytic reaction after phosphinothricin dehydrogenase site-saturation mutagenesis

| 164$^{th}$ site mutation of phosphinothricin dehydrogenase | Conversion (%) | 205$^{th}$ mutation of phosphinothricin dehydrogenase | Conversion (%) |
|---|---|---|---|
| WT | 11.5 | WT | 11.5 |
| A164R | N.D. | R205A | N.D. |
| A164N | 1.2 | R205N | 1.6 |
| A164D | N.D. | R205D | N.D. |
| A164C | 4.3 | R205C | N.D. |
| A164Q | 5.7 | R205Q | 3.4 |
| A164E | N.D. | R205E | N.D. |
| A164G | 63.6 | R205G | N.D. |
| A164H | N.D. | R205H | 10.8 |
| A164I | 10.4 | R205I | N.D. |
| A164L | 9.9 | R205L | N.D. |
| A164K | N.D. | R205K | 21.3 |
| A164M | 7.3 | R205M | 2.6 |
| A164F | N.D. | R205F | N.D. |
| A164P | N.D. | R205P | N.D. |
| A164S | N.D. | R205S | N.D. |
| A164T | N.D. | R205T | 2.9 |
| A164W | 3.0 | R205W | N.D. |
| A164Y | N.D. | R205Y | N.D. |
| A164V | 10.9 | R205V | N.D. |

N.D.: not detected

As can be seen from Table 2, phosphinothricin dehydrogenase mutant A164G can increase the conversion of 300 mM PPO from 11.5% to 63.6% without exogenous NADP$^+$. However, no other strain with increased activity was screened out through A164 site-saturation mutagenesis and screening. The phosphinothricin dehydrogenase mutant R205K increased the conversion of 300 mM PPO from 11.5% to 21.3% without exogenous NADP$^+$. However, no other strain with increased activity was screened out through R205 site-saturation mutagenesis and screening. Then, the A164G and R205K mutation sites were mutated together, and the results showed that the activity was further improved, and the conversion of 300 mM PPO reached 68.1%.

In addition to the error-prone PCR technology, phosphinothricin dehydrogenase was also subjected to homology modeling and molecular docking according to semi-rational design, and some other mutation sites with potentially improved activity were selected for site-saturation mutagenesis. Homology modeling: with the protein crystal structure with the highest homology with phosphinothricin dehydrogenase found in the PDB database as a template, homology modeling was performed using Modeller 9.22, molecular docking was conducted using autock vina, appropriate mutation sites were selected, mutation primers were designed, site-saturation mutagenesis was conducted, and high-throughput screening was carried out.

After many times of site-saturation mutagenesis and screening, the mutant PPTDH-T332A with improved activity was finally screened out. The activity of the three-enzyme mutant A164G_R205K_T332A was further improved compared with that of the wild type, and the conversion of 300 mM PPO reached 71.2%. Therefore, the phosphinothricin mutant A164G_R205K_T332A was finally selected.

EXAMPLE 4

Overexpression of Glucose Dehydrogenase in the Multi-enzyme Coupling Reaction System On the double enzyme coupling expression vector pET-Duet-1, the expression level of EsGDH protein was not high, resulting in poor coenzyme circulation efficiency. A strain with improved activity was screened out in Example 2, which was attributable to the deletion of bases between the second cloning site RBS and glucose dehydrogenase. Therefore, it is deduced that the expression level of GDH is related to the length of bases between glucose dehydrogenase and RBS sequence. Thus, the length of bases between glucose dehydrogenase and RBS sequence was further optimized. The primer design is shown in Table 3, and the experimental results are shown in Table 4.

TABLE 3

Design of primers with optimized number of bases in multi-enzyme catalytic reaction

| Primer name | Primer sequence |
| --- | --- |
| 10bp-F | TATAATTCATATACATCCATGGGTTATAATTC |
| 10bp-R | GAATTATAACCCATGGATGTATATGAATTATA |
| 8bp-F | TATAATTCATATACATATGGGTTATAATTC |
| 8bp-R | GAATTATAACCCATATGTATATGAATTATA |
| 6bp-F | TATAATTCATATACATGGGTTATAATTC |
| 6bp-R | GAATTATAACCCATGTATATGAATTATA |
| 4bp-F | TATAATTCATATATGGGTTATAATTC |
| 4bp-R | GAATTATAACCCATATATGAATTATA |

TABLE 4

Summary of conversion after base number optimization in multi-enzyme catalytic reaction

| Number | Linker sequence (5'-3') | Linking length (bp) | Conversion (%) |
| --- | --- | --- | --- |
| 1 | ATATACATCCAGAT | 14 | 11.5 |
| 2 | ATATACATCCAGA | 13 | 35.1 |
| 3 | ATATACATCC | 10 | 78.8 |
| 4 | ATATACAT | 8 | 99.1 |
| 5 | ATATAC | 6 | 26.0 |
| 6 | ATAT | 4 | 4.3 |

Figure 5:
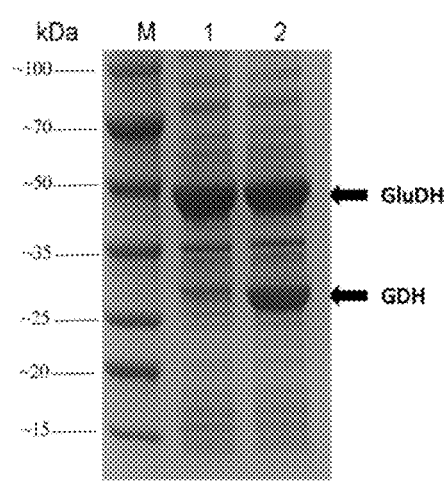
FIG. 5 is a SDS-PAGE diagram of the PPTDH and EsGDH double enzyme coupling in Example 4, wherein Lane 1: protein ladder; Lane 2: recombinant E. coli cells prior to overexpression of EsGDH; Lane 3: recombinant E. coli cells after overexpression of EsGDH.

As shown in Table 4, when the length of bases between glucose dehydrogenase and RBS sequence was 8 bp, the expression of EsGDH gene was significantly improved. See FIG. 5 for SDS-PAGE analysis. The efficiency of double enzyme coupling catalysis was greatly improved, and the conversion of 300 mM PPO reached 99.1%.

EXAMPLE 5

Measurement and Comparison of Total Turnover Number (TTN) in PPO Amination

The total turnover number in PPO amination was detected to show the catalytic efficiency of wild-type and mutant phosphinothricin dehydrogenase, and coupled wild-type and mutant PPTDH-EsGDH double enzymes. In the case of wild-type and mutant phosphinothricin dehydrogenase alone, the reaction system was: 100 mM PPO, 0.5 mM NADPH, 400 mM $NH_4^+$, 0.5 g/L stem cells. In the case of coupled phosphinothricin dehydrogenase and glucose dehydrogenase, additional 120 mM glucose was required in the reaction system. After 5 minutes of reaction, samples of the reaction mixture were processed and the concentration of L-PPT was determined by HPLC.

The calculation formula of TTN (μmol L-PPT/μmol catalyst) for single enzyme or multiple enzymes is as follows:

$$TTN = (L\text{-}PPT\ (mol/L))/(PPTDH\ (g/L)\cdot 49060\ (mol/g))$$

TABLE 5

TTN values for the wild-type and mutant A164G_R205K_T332A of three different enzymes

| | | TTN | |
| --- | --- | --- | --- |
| Number | Enzyme | $WT^{NADPH}$ | $A164G\_R205K\_T332A^{NADPH}$ |
| 1 | PPTDH alone | 115 ± 7 | 168 ± 12 |
| 2 | PPTDH + low expressed EsGDH | 281 ± 13 | 5846 ± 143 |
| 3 | PPTDH + high expressed EsGDH | 547 ± 35 | 33950 ± 238 |

As can be seen from the data in Table 5, when PPTDH alone was used without the NAPDH regeneration system (EsGDH), the TTN remained at a low level, and the TTN values for PPTDH_WT and the variant PPTDH_A164G_R205K_T332A were less than 200. The TTN increased to 5846 when PPTDH_A164G_R205K_T332A was coupled with low expressed EsGDH to catalyze the reaction; and the TTN reached the maximum of 33950 when PPTDH_A164G_R205K_T332 was coupled with high expressed EsGDH to catalyze the reaction, indicating that preparation of L-PPT through catalytic reaction with coupled PPTDH_A164G_R205K_T332A and high expressed EsGDH reached the optimal coupling efficiency.

EXAMPLE 6

Site-saturation Mutagenesis of Formate Dehydrogenase in Multi-enzyme Coupling Reaction System First, NADP+ dependent formate dehydrogenase derived from *Lactobacillus buchneri* was obtained by gene mining. Considering that the original enzyme activity was low, the semi-rational design of homology modeling and molecular docking was used to select the appropriate mutation sites, and site-saturation mutagenesis was used to screen mutants with enhanced activity. The determined mutation sites were S148, Q222, R223, H224, M334, T338, K380 and T383.

An NADPH high throughput screening method was established. Since the molar extinction coefficient (ε) of NADPH is large at 340 nm and always stands at 6220 L mol$^{-1}$cm$^{-1}$, the $OD_{340}$ is in direct proportion to the concentration of NADPH, and thus the enzyme activity can be determined by determining the value of $OD_{340}$ in the reaction mixture. The reaction system for determining enzyme activity was 1 ml, containing 100 mM ammonium formate, 1 mM NADP+, 100 mM phosphate buff (pH=7), and an appropriate amount of bacterial cells, and the reaction temperature was 30° C.

TABLE 6

Design of primers for site-saturation mutagenesis of formate dehydrogenase in multi-enzyme coupling reaction system

| Primer name | Primer sequence |
| --- | --- |
| FDH-S148-F | GAAGTGACCTATAGCAATNNKGTTAGTGTTGC |
| FDH-S148-R | CTGCTTCTGCAACACTAACMNNATTGCTATAG |
| FDH-Q222-F | CGTTAAACTGGTGTATAATNNKCGCCATCAGC |
| FDH-Q222-R | CCGGCAGCTGATGGCGMNNATTATACACC |
| FDH-R223-F | CTGGTGTATAATCAGNNKCATCAGCTGCCG |
| FDH-R223-R | CTTCATCCGGCAGCTGATGMNNCTGATTATAC |
| FDH-H224-F | GGTGTATAATCAGCGCNNKCAGCTGCCGG |
| FDH-H224-R | CAACTTCATCCGGCAGCTGMNNGCGCTGATTA |
| FDH-M334-F | GAAGCAATGACCCCGCATNNKAGTGGCACC |
| FDH-M334-R | CTCAGGGTGGTGCCACTMNNATGCGGGGTC |
| FDH-T338-F | CCCGCATATGAGTGGCACCNNKCTGAGTGCC |
| FDH-T338-R | GCGTGCCTGGGCACTCAGMNNGGTGCCACTC |
| FDH-K380-F | GGCCGGTACCGGTGCCNNKAGTTATACCG |
| FDH-K380-R | CCTTTTTTCACGGTATAACTMNNGGCACCGG |
| FDH-T383-F | CGGTGCCAAAAGTTATNNKGTGAAAAAAGG |
| FDH-T383-R | GGTTTCTTCGCCTTTTTTCACMNNATAACTTT |

The results of high-throughput screening showed that most of the mutants were nonsense mutations, only H224Q was a beneficial mutation site, and the relative enzyme activity of formate dehydrogenase was increased by 23%.

EXAMPLE 7

Expression and Purification of Phosphinothricin Dehydrogenase

1. Wet cells containing phosphinothricin dehydrogenase gene and glucose dehydrogenase gene: The recombinant *E. coli* BL21(DE3)/PET Duet-PPT GDH-ES GDH obtained in Example 1 was inoculated into an LB liquid medium containing 50 μg/mL ampicillin resistance to culture at 37° C. and 200 rpm for 12 hours, and then inoculated at an inoculum size of 1% (v/v) into a fresh LB liquid medium containing 50 μg/ml ampicillin resistance to culture at 37° C. and 150 rpm until the $OD_{600}$ of the cells reached 0.6-0.8. Then, IPTG with a final concentration of 0.1 mM was added to induce and culture at 22° C. for 16 hours. The mixture was then centrifuged at 4° C. and 8,000 rpm for 20 minutes, and the supernatant was discarded. The precipitate was collected, and washed with 20 mM phosphate buffer (PBS) at pH 7.5 two times to obtain wet cells of recombinant strain *E.coli* BL21(DE3)/pETDuet-PPTGDH-EsGDH containing phosphinothricin dehydrogenase gene and glucose dehydrogenase gene. The wet cells were re-suspended in 100 mM PBS at pH 7.5, and ultrasonically crushed on an ice-water mixture for 10 minutes (ultrasonic crushing conditions: 400 W, crushing for 1 second with an interval of 5 seconds) to obtain crude enzyme.

Figure 6:
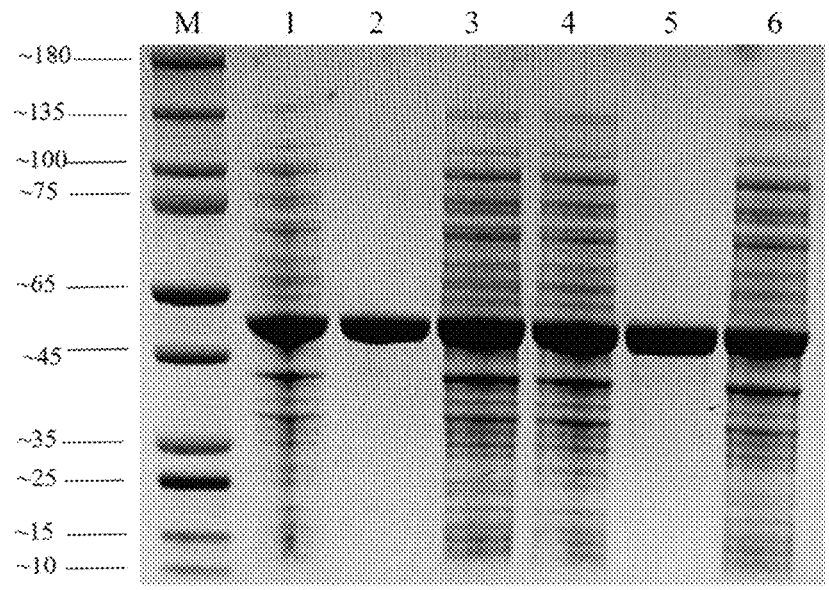
FIG. 6 is a SDS-PAGE diagram of wild-type phosphinothricin dehydrogenase and mutant phosphinothricin dehydrogenase. Lane M: protein ladder; Lane 1: crude wild-type phosphinothricin dehydrogenase supernatant; Lane 2: purified wild-type phosphinothricin dehydrogenase; Lane 3: E. coli containing wild-type phosphinothricin dehydrogenase; Lane 4: crude phosphinothricin dehydrogenase mutant A164G_R205K_T332A supernatant; Lane 5: purified phosphinothricin dehydrogenase mutant A164G_R205K_T332A; Lane 6: E. coli containing phosphinothricin dehydrogenase mutant A164G_R205K_T332A.

The crude enzyme was centrifuged at 4° C. and 12,000 rpm for 20 minutes and the supernatant was collected. The mutant protein was purified using a Ni affinity column (1.6×10 cm, Bio-Rad, USA) by steps of: (1) equilibrating the Ni column with 5 column volumes of a binding buffer (50 mM sodium phosphate buffer containing 0.3 M NaCl, pH 8.0,) until stable baseline; (2) loading the sample at a flow rate of 1 mL/min at a loading amount of 25-40 mg/mL protein so that the target protein is adsorbed on the Ni column; (3) washing out miscellaneous proteins with six column volumes of buffer A (50 mM sodium phosphate buffer containing 0.3 M NaCl and 30 mM imidazole, pH 8.0) at a flow rate of 1 mL/min until stable baseline; and (4) eluting with buffer B (50 mM sodium phosphate buffer containing 0.3 M NaCl and 500 mM imidazole, pH 8.0) at a flow rate of 1 mL/min, and collecting the target protein. The target protein was dialyzed overnight in 20 mM phosphate buffer at pH 7.5 to obtain the purified enzyme. The electrophoresis pattern is shown in FIG. 6.

LB culture medium: 10 g/L tryptone, 5 g/L yeast extract, and 10 g/L sodium chloride in distilled water as the solvent, pH 7.4.

LB plate: 10 g/L tryptone, 5 g/L yeast extract, 10 g/L sodium chloride, 18 g/L agar in distilled water as the solvent, pH 7.4.

EXAMPLE 8

Determination of Kinetic Parameters of Wild-type Phosphinothricin Dehydrogenase and its Mutant Reaction system: substrate PPO concentration 2-30 mM, 50 mM ammonium sulfate, 1-15 mM NADPH and a certain amount of purified enzyme; reaction medium: 100 mM phosphate buffer (pH 7.0); reaction temperature: 40° C. The obtained initial velocity data is fitted to the following equation:

$$V = \frac{V\max[A][B]}{[A][B] + [B]Km^A + [A]Km^B + Km^B \bullet Ks^A}$$

where [A] and [B] are the concentrations of NADPH and PPO respectively, and $Km^A$ and $Km^B$ are the apparent substrate affinities for NADPH and PPO respectively. Vmax is the maximum reaction rate of the enzyme when the substrate reaches saturation, and $Ks^A$ represents the dissociation constant between phosphinothricin dehydrogenase and NADPH.

TABLE 7

Dynamics parameters of wild-type phosphinothricin dehydrogenase and its mutant (A164G_R205K_T332A)

| Enzyme | $K_m^A$ (nM) | $K_m^B$ (mM) | $k_{cat}$ (s$^{-1}$) | $k_{cat}/K_m^A$ (s$^{-1}$ mM$^{-1}$) | $k_{cat}/K_m^B$ (s$^{-1}$ mM$^{-1}$) |
|---|---|---|---|---|---|
| WT | 0.14 ± 0.02 | 6.12 ± 0.32 | 7.47 ± 0.22 | 53.36 | 1.22 |
| A164G_R205K_T332A | 0.09 ± 0.01 | 5.35 ± 0.28 | 951.85 ± 20.4 | 10576.11 | 177.92 |

As can be seen from the data in Table 7, the catalytic constant ($k_{cat}$) of the phosphinothricin dehydrogenase mutant A164G_R205K_T332A was significantly increased from 7.47 s$^{-1}$ (WT) to 951.85 s$^{-1}$ (A164G_R205K_T332A), and the substrate affinity of the phosphinothricin dehydrogenase mutant A164G_R205K_T332A was slightly higher than that of WT ($K_m$: 5.35 mM versus 6.12 mM). High $k_{cat}$ and moderate substrate affinity resulted in very high catalytic efficiency ($k_{cat}/K_m$) for PPO, which was significantly increased from 1.22 s$^{-1}$mM$^{-1}$ (WT) to 177.92 s$^{-1}$mM$^{-1}$ (A164G_R205K_T332A), so that the catalytic efficiency of the phosphinothricin dehydrogenase mutant A164G_R205K_T332A was increased 145.83 times compared with that of the wild type.

EXAMPLE 9

Figure 7:
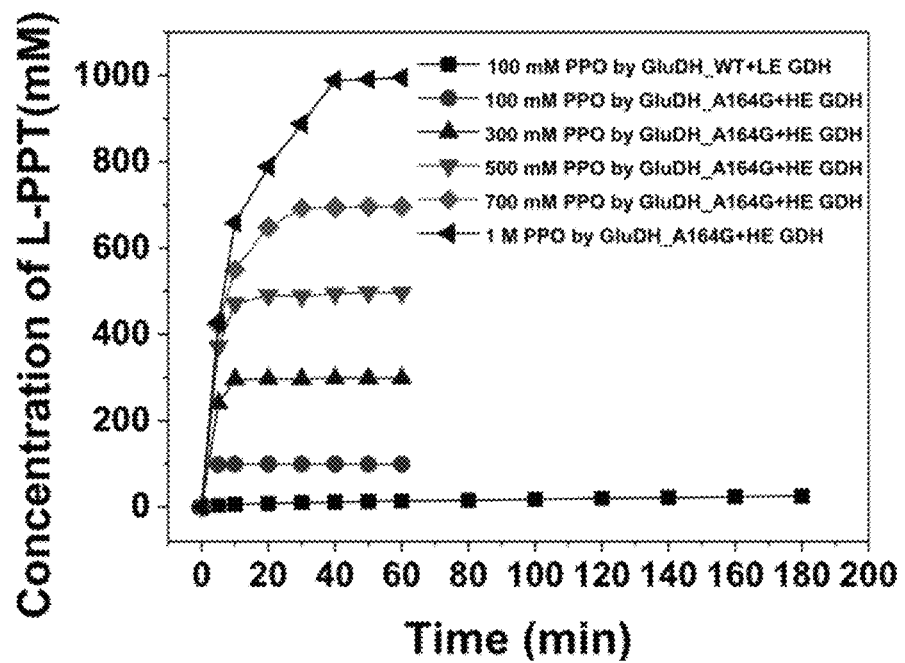
FIG. 7 is a reaction process diagram showing synthesis of L-PPT by asymmetric reductive amination using recombinant E. coli BL21(DE3)/pETDuet-PPTDH-EsGDH, where 0.5 mM NADP+ coenzyme is additionally added in the reaction system; reaction conditions: 40° C., pH=7.5. LE: low expression; HE: high expression.

Synthesis of L-PPT by Asymmetric Reductive Amination Using Recombinant E. Coli BL21(DE3)/pETDuet-1-PPTDH_A164G_R205K_T332A-EsGDH/LbFDH_H224Q The reaction system consisted of 100 mM-1 M PPO, 120 mM-1.2 M glucose, 150 mM-1 M ammonium sulfate, 0.5 mM NADP$^+$, recombinant E. coli BL21(DE3)/pETDuet-1-PPTDH_A164G_R205K_T332A-EsGDH (high expression) (0.5g/L stem cells). Reaction conditions: thermostatic water bath at 40° C. and rotating speed of 500 rpm. During the whole reaction process, the pH value of the reaction mixture was controlled to be 7.5 by feeding NH$_3$.H$_2$O. Samples (100 µl) were taken at regular intervals, the reaction was stopped by adding 5 µL of 6 M concentrated hydrochloric acid, and the samples were then processed to determine conversion by measuring the concentration of L-PPT by HPLC, with the reaction progress curve shown in FIG. 7.

When the concentration of PPO substrate was 100 mM, the substrate could be completely converted into L-PPT (conversion >99% and e.e.>99%) in 5 minutes with 0.5 g·L$^{-1}$ catalyst. Under the same reaction conditions, using the original cells (phosphinothricin dehydrogenase WT and low expressed EsGDH), the conversion could only reach about 26% (25.68 mM after 3 hours). When the concentration of PPO substrate increased to 500 mM (89.04 g·L$^{-1}$) and 1 M (178.08 g·L$^{-1}$), using 0.5g·L$^{-1}$ catalyst, the substrate could be completely converted after 20 minutes and 40 minutes respectively, with e.e.>99%. The space-time yield (STY) of the latter reached 7110 g·L$^{-1}$·d$^{-1}$, 173 times higher than that of the original strain (37 g·L$^{-1}$·d$^{-1}$). Phosphinothricin dehydrogenase coupled with glucose dehydrogenase still showed the highest conversion and the shortest reaction time compared with the reactions catalyzed by amidase and transaminase, as shown in Table 8.

TABLE 8

Comparison with the preparation of L-PPT through modified enzyme as reported in other publications

| Biocatalyst | Substrate | Substrate concentration (g/L) | Catalyst concentration (g/L) | Reaction time (h) | Conversion (%) | e.e. (100%) | Space-time yield g·L$^{-1}$·d$^{-1}$ |
|---|---|---|---|---|---|---|---|
| Amidase[a] | rac-S[d] | 150 | 0.03 | 6.8 | 49.7 | >99 | 263.1 |
| Transaminase[b] | PPO | 20 | 34 | 14 | 91.2 | >99 | 31.3 |
| GluDH_I170M[c] | PPO | 53.4 | five | 36 | 95 | >99 | 33.8 |
| LsGluDH_A175G[c] | PPO | 89.04 | 0.5 | 1.5 | 99 | >99 | 1482.9 |
| PPTDH_A164G_R205K_T332A coupled with over-expressed EsGDH[c] | PPO | 178.08 | 0.5 | 0.67 | 99 | >99 | 7110 |

Notes:
[a]purified amidase as catalyst;
[b]immobilized transaminases as catalyst;
[c]stem cells as catalysts;
[d]racemic-4-[hydroxy(methyl)phosphoryl]-2-(2-phenylacetamido)butyric acid.

Reaction system: 400 mM PPO, 800 mM ammonium formate, recombinant E. coli BL21(DE3)/pETDuet-1-PPTDH_A164G_R205K_T332A-LbFDH_H224Q, 25 g·L$^{-1}$ catalyst. Reaction conditions: thermostatic water bath at 45° C. and rotating speed of 600 rpm. The changes in the concentration and e.e. value of the product L-PPT during the reaction were detected by HPLC.

The results showed that the product concentration increased gradually with the passage of time, the reaction was completed within 3.5 hours, the substrate conversion was greater than 99%, and the e.e. value of the product remained above 99.5%.

What is claimed is:

1. A phosphinothricin dehydrogenase mutant, wherein the phosphinothricin dehydrogenase mutant has the amino acid sequence of SEQ ID NO: 1.

2. A polynucleotide comprising a nucleotide sequence encoding the phosphinothricin dehydrogenase mutant according to claim 1.

3. A recombinant bacterium comprising the polynucleotide according to claim 2.

4. The recombinant bacterium according to claim 3, wherein the polynucleotide further comprises a nucleotide sequence encoding a glucose dehydrogenase or a formate dehydrogenase.

5. The recombinant bacterium according to claim 4, wherein the recombinant bacterium comprises a double gene expression vector, and wherein the nucleotide sequence encoding the phosphinothricin dehydrogenase mutant is cloned into a first polyclonal site region of the double gene expression vector, and the nucleotide sequence encoding the glucose dehydrogenase or the formate dehydrogenase is cloned into a second polyclonal site region of the double gene expression vector.

6. The recombinant bacterium according to claim 5, wherein the nucleotide sequence encoding the glucose dehydrogenase is derived from *Exiguobacterium sibiricum*, and the length of linking bases between an initiation codon of the nucleotide sequence encoding the glucose dehydrogenase and the corresponding ribosome binding site on a plasmid is 8-10 bp.

7. The recombinant bacterium according to claim 5, wherein the nucleotide sequence encoding the formate dehydrogenase has the nucleotide sequence as shown in SEQ ID NO: 3.

8. A method for preparing L-phosphinothricin, comprising the step of reacting 2-carbonyl-4-(hydroxymethylphosphinic) butyric acid as a substrate and glucose or ammonium formate as a co-substrate with a catalyst in the presence of an inorganic amino donor and a coenzyme regeneration system to obtain L-phosphinothricin;

wherein the coenzyme regeneration system is a glucose dehydrogenase regeneration system or a formate dehydrogenase regeneration system; and the catalyst comprises the recombinant bacterium according to claim 5 or a phosphinothricin dehydrogenase mutant having the amino acid sequence of SEQ ID NO: 1.

* * * * *